(12) United States Patent
Pfander et al.

(10) Patent No.: US 9,880,314 B2
(45) Date of Patent: Jan. 30, 2018

(54) METHODS FOR IMPROVING PROCESSING SPEED FOR OBJECT INSPECTION

(71) Applicant: Rapiscan Systems, Inc., Torrance, CA (US)

(72) Inventors: Andreas Pfander, Torrance, CA (US); Ronald James Hughes, Garden Grove, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 14/338,435

(22) Filed: Jul. 23, 2014

(65) Prior Publication Data

US 2015/0030125 A1 Jan. 29, 2015

Related U.S. Application Data

(60) Provisional application No. 61/857,688, filed on Jul. 23, 2013.

(51) Int. Cl.
*G01V 5/00* (2006.01)
*G01N 23/04* (2006.01)

(52) U.S. Cl.
CPC ........... *G01V 5/0016* (2013.01); *G01N 23/04* (2013.01); *G01V 5/0008* (2013.01)

(58) Field of Classification Search
CPC .... G01V 5/0008; G01V 5/0041; G01V 5/005; G01V 5/0058; G01V 5/0066; G01N 23/04; G01N 23/046
USPC ...................................................... 378/53, 57
See application file for complete search history.

(56) References Cited

U.S. PATENT DOCUMENTS

| 2,636,619 A | 4/1953 | Alexander |
| 3,275,831 A | 9/1966 | Martin |
| 3,374,355 A | 3/1968 | Parratt |
| 3,439,166 A | 4/1969 | Chope |
| 3,837,502 A | 9/1974 | Hornagold |

(Continued)

FOREIGN PATENT DOCUMENTS

| EP | 0077018 A1 | 4/1983 |
| EP | 0919186 A2 | 6/1999 |

(Continued)

OTHER PUBLICATIONS

International Search Report for PCT/US2015/040653, dated Dec. 16, 2015.

(Continued)

*Primary Examiner* — Allen C. Ho
(74) *Attorney, Agent, or Firm* — Novel IP

(57) ABSTRACT

The present specification describes methods and systems for inspecting objects by means of penetrating radiation where objects are conveyed through the penetrating radiation and subsequent images of objects are reviewed by an operator. Specifically, the present specification describes a system that decouples the synchronization between cessation of image generation on the display and image acquisition through conveyance of the article. Further, the present specification discloses methods for compensating for image acquisition inefficiencies involving article separation by the queuing conveyor and the post-stop back belt process, resulting in throughput enhancement.

13 Claims, 8 Drawing Sheets

(56) References Cited

U.S. PATENT DOCUMENTS

| | | | |
|---|---|---|---|
| 3,904,923 A | 9/1975 | Schwartz | |
| 4,164,138 A | 8/1979 | Burkhart | |
| 4,239,969 A | 12/1980 | Galetta | |
| 4,658,408 A | 4/1987 | Amor | |
| 5,014,293 A | 5/1991 | Boyd | |
| 5,041,728 A | 8/1991 | Spacher | |
| 5,065,418 A | 11/1991 | Bermbach | |
| 5,181,234 A | 1/1993 | Smith | |
| 5,182,764 A * | 1/1993 | Peschmann | G01V 5/005 250/442.11 |
| 5,185,778 A | 2/1993 | Magram | |
| 5,197,088 A | 3/1993 | Vincent | |
| 5,202,932 A | 4/1993 | Cambier | |
| 5,259,012 A | 11/1993 | Baker | |
| 5,363,940 A | 11/1994 | Fahrion | |
| 5,367,552 A * | 11/1994 | Peschmann | G01V 5/005 376/159 |
| 5,493,596 A | 2/1996 | Annis | |
| 5,503,424 A | 4/1996 | Agopian | |
| 5,600,303 A | 2/1997 | Husseiny | |
| 5,600,700 A * | 2/1997 | Krug | G01N 23/201 376/159 |
| 5,606,167 A | 2/1997 | Miller | |
| 5,642,393 A * | 6/1997 | Krug | G01V 5/0016 376/159 |
| 5,692,028 A | 11/1997 | Geus | |
| 5,692,029 A | 11/1997 | Husseiny | |
| 5,699,400 A * | 12/1997 | Lee | G01V 5/0008 378/57 |
| 5,842,578 A | 12/1998 | Cordeiro | |
| 5,909,478 A | 6/1999 | Polichar | |
| 5,974,111 A * | 10/1999 | Krug | G01N 23/20 378/53 |
| 6,056,671 A | 5/2000 | Marmer | |
| 6,081,580 A | 6/2000 | Grodzins | |
| 6,088,423 A * | 7/2000 | Krug | G01V 5/0016 378/4 |
| 6,172,712 B1 * | 1/2001 | Beard | H04N 5/4401 348/143 |
| 6,216,540 B1 | 4/2001 | Nelson | |
| 6,218,943 B1 * | 4/2001 | Ellenbogen | G01V 5/0008 340/572.1 |
| 6,220,099 B1 | 4/2001 | Marti | |
| 6,236,709 B1 * | 5/2001 | Perry | G01N 23/046 378/25 |
| 6,249,567 B1 | 6/2001 | Rothschild | |
| 6,292,533 B1 | 9/2001 | Swift | |
| 6,301,327 B1 | 10/2001 | Martens | |
| 6,304,629 B1 * | 10/2001 | Conway | G01N 23/04 198/502.1 |
| 6,347,132 B1 | 2/2002 | Annis | |
| 6,418,194 B1 | 7/2002 | McPherson | |
| 6,430,255 B2 * | 8/2002 | Fenkart | G01N 23/046 378/203 |
| 6,459,761 B1 | 10/2002 | Grodzins | |
| 6,459,764 B1 | 10/2002 | Chalmers | |
| 6,473,487 B1 * | 10/2002 | Le | G01N 23/04 378/57 |
| 6,542,574 B2 | 4/2003 | Grodzins | |
| 6,542,580 B1 | 4/2003 | Carver | |
| 6,552,346 B2 | 4/2003 | Verbinski | |
| 6,567,496 B1 * | 5/2003 | Sychev | G01N 23/04 378/57 |
| 6,614,872 B2 | 9/2003 | Bueno | |
| 6,653,588 B1 * | 11/2003 | Gillard-Hickman | B65G 13/10 198/369.4 |
| 6,665,373 B1 | 12/2003 | Kotowski | |
| 6,702,459 B2 | 3/2004 | Barnes | |
| 6,713,773 B1 | 3/2004 | Lyons | |
| 6,843,599 B2 | 1/2005 | Le | |
| 6,856,667 B2 * | 2/2005 | Ellengogen | G01V 5/0025 378/189 |
| 6,920,197 B2 | 7/2005 | Kang | |
| 6,924,487 B2 | 8/2005 | Bolozdynya | |
| 6,928,141 B2 | 8/2005 | Carver | |
| 6,988,610 B2 * | 1/2006 | Fromme | B65G 43/02 198/502.1 |
| 7,012,256 B1 * | 3/2006 | Roos | G01V 5/0083 250/358.1 |
| 7,046,768 B1 | 5/2006 | Gilevich | |
| 7,072,434 B1 * | 7/2006 | Tybinkowski | G01N 23/046 378/203 |
| 7,151,447 B1 | 12/2006 | Willms | |
| 7,151,817 B1 * | 12/2006 | Abraham | G01N 23/046 378/208 |
| 7,164,747 B2 * | 1/2007 | Ellenbogen | G01N 23/046 378/19 |
| 7,203,276 B2 | 4/2007 | Arsenault | |
| 7,207,713 B2 | 4/2007 | Lowman | |
| 7,215,738 B2 | 5/2007 | Muenchau | |
| 7,286,634 B2 * | 10/2007 | Sommer, Jr. | B64F 1/368 250/359.1 |
| 7,317,390 B2 * | 1/2008 | Huey | G01V 5/0008 340/522 |
| 7,322,745 B2 | 1/2008 | Agrawal | |
| 7,366,281 B2 * | 4/2008 | Skatter | G01V 5/0016 340/531 |
| 7,366,282 B2 | 4/2008 | Peschmann | |
| 7,369,643 B2 | 5/2008 | Kotowski | |
| 7,379,530 B2 | 5/2008 | Hoff | |
| 7,397,891 B2 | 7/2008 | Johnson | |
| 7,400,701 B1 | 7/2008 | Cason | |
| 7,417,440 B2 | 8/2008 | Peschmann | |
| 7,418,077 B2 | 8/2008 | Gray | |
| 7,453,987 B1 | 11/2008 | Richardson | |
| 7,471,764 B2 * | 12/2008 | Kaval | G01N 23/04 378/57 |
| 7,483,510 B2 | 1/2009 | Carver | |
| 7,486,768 B2 | 2/2009 | Allman | |
| 7,492,860 B2 * | 2/2009 | Garms | G01N 23/046 378/4 |
| 7,517,149 B2 | 4/2009 | Agrawal | |
| 7,519,148 B2 | 4/2009 | Kotowski | |
| 7,525,101 B2 | 4/2009 | Grodzins | |
| 7,526,064 B2 | 4/2009 | Akery | |
| 7,558,370 B2 * | 7/2009 | Sommer, Jr. | G01V 5/0016 378/57 |
| 7,579,845 B2 | 8/2009 | Peschmann | |
| 7,606,348 B2 * | 10/2009 | Foland | G01N 23/046 378/4 |
| 7,660,388 B2 | 2/2010 | Gray | |
| 7,720,194 B2 * | 5/2010 | Connelly | G01V 5/0016 378/57 |
| 7,720,195 B2 | 5/2010 | Allman | |
| 7,742,568 B2 | 6/2010 | Smith | |
| 7,769,133 B2 | 8/2010 | Carver | |
| 7,783,004 B2 | 8/2010 | Kotowski | |
| 7,783,005 B2 | 8/2010 | Kaval | |
| 7,817,776 B2 | 10/2010 | Agrawal | |
| 7,856,081 B2 | 12/2010 | Peschmann | |
| 7,860,213 B2 | 12/2010 | Akery | |
| 7,869,566 B2 * | 1/2011 | Edic | G01V 5/0041 378/57 |
| 7,876,879 B2 | 1/2011 | Morton | |
| 7,876,880 B2 | 1/2011 | Kotowski | |
| 7,881,426 B2 * | 2/2011 | Basu | G01V 5/005 378/15 |
| 7,899,232 B2 * | 3/2011 | Gudmundson | G06K 9/6255 356/240.1 |
| 7,915,596 B2 | 3/2011 | Clothier | |
| 7,928,400 B1 | 4/2011 | Diawara | |
| 7,963,695 B2 | 6/2011 | Kotowski | |
| 7,982,191 B2 | 7/2011 | Friedman | |
| 7,991,133 B2 | 8/2011 | Mills | |
| 7,995,705 B2 | 8/2011 | Allman | |
| 8,047,053 B2 * | 11/2011 | Call | G01N 1/2202 73/28.01 |
| 8,054,938 B2 | 11/2011 | Kaval | |
| 8,059,781 B2 | 11/2011 | Agrawal | |
| 8,073,099 B2 | 12/2011 | Niu | |

(56) References Cited

U.S. PATENT DOCUMENTS

| | | | |
|---|---|---|---|
| 8,090,150 B2 * | 1/2012 | Garms | G01V 5/0016 378/57 |
| 8,135,110 B2 | 3/2012 | Morton | |
| 8,138,770 B2 | 3/2012 | Peschmann | |
| 8,170,177 B2 | 5/2012 | Akery | |
| 8,243,876 B2 | 8/2012 | Morton | |
| 8,275,091 B2 | 9/2012 | Morton | |
| 8,356,937 B2 | 1/2013 | Kotowski | |
| 8,385,501 B2 | 2/2013 | Allman | |
| 8,389,942 B2 | 3/2013 | Morton | |
| 8,428,217 B2 | 4/2013 | Peschmann | |
| 8,433,036 B2 | 4/2013 | Morton | |
| 8,457,275 B2 | 6/2013 | Akery | |
| 8,483,356 B2 | 7/2013 | Bendahan | |
| 8,491,189 B2 | 7/2013 | Kotowski | |
| 8,503,605 B2 | 8/2013 | Morton | |
| 8,579,506 B2 | 11/2013 | Morton | |
| 8,644,453 B2 | 2/2014 | Morton | |
| 8,668,386 B2 | 3/2014 | Morton | |
| 8,674,706 B2 | 3/2014 | Peschmann | |
| 8,687,765 B2 | 4/2014 | Kotowski | |
| 8,735,833 B2 | 5/2014 | Morto | |
| 8,750,452 B2 | 6/2014 | Kaval | |
| 8,774,357 B2 | 7/2014 | Morton | |
| 8,798,232 B2 | 8/2014 | Bendahan | |
| 8,805,011 B2 * | 8/2014 | Delianski | G01V 5/0016 382/103 |
| 8,831,176 B2 | 9/2014 | Morto | |
| 8,837,670 B2 | 9/2014 | Akery | |
| 8,840,303 B2 | 9/2014 | Morton | |
| 8,879,791 B2 * | 11/2014 | Drouin | G01N 23/046 378/57 |
| 8,908,831 B2 | 12/2014 | Bendahan | |
| 8,929,509 B2 | 1/2015 | Morton | |
| 8,958,526 B2 | 2/2015 | Morton | |
| 8,971,485 B2 | 3/2015 | Morton | |
| 8,993,970 B2 | 3/2015 | Morton | |
| 9,014,425 B2 * | 4/2015 | Perron | G01V 5/0016 250/358.1 |
| 9,020,095 B2 | 4/2015 | Morton | |
| 9,020,096 B2 | 4/2015 | Allman | |
| 9,025,731 B2 | 5/2015 | Kotowski | |
| 9,042,511 B2 | 5/2015 | Peschmann | |
| 9,052,403 B2 | 6/2015 | Morton | |
| 9,057,679 B2 | 6/2015 | Morton | |
| 9,086,497 B2 | 7/2015 | Bendahan | |
| 9,111,331 B2 | 8/2015 | Parikh | |
| 9,121,958 B2 | 9/2015 | Morton | |
| 9,158,027 B2 | 10/2015 | Morton | |
| 9,218,933 B2 | 12/2015 | Langeveld | |
| 9,223,049 B2 | 12/2015 | Kotowski | |
| 9,223,050 B2 | 12/2015 | Kaval | |
| 9,223,052 B2 | 12/2015 | Morton | |
| 9,268,058 B2 | 2/2016 | Peschmann | |
| 9,274,065 B2 | 3/2016 | Morton | |
| 9,279,901 B2 | 3/2016 | Akery | |
| 9,285,498 B2 | 3/2016 | Carver | |
| 9,310,322 B2 | 4/2016 | Panesar | |
| 9,310,323 B2 | 4/2016 | Bendahan | |
| 9,316,760 B2 | 4/2016 | Bendahan | |
| 9,329,285 B2 | 5/2016 | Gozani | |
| 9,332,624 B2 | 5/2016 | Morton | |
| 2002/0094064 A1 | 7/2002 | Zhou | |
| 2003/0043964 A1 | 3/2003 | Sorenson | |
| 2003/0068557 A1 | 4/2003 | Kumashiro | |
| 2004/0051265 A1 | 3/2004 | Nadeau | |
| 2004/0120454 A1 | 6/2004 | Ellenbogen | |
| 2004/0141584 A1 | 7/2004 | Bernardi | |
| 2004/0252024 A1 | 12/2004 | Huey | |
| 2004/0258198 A1 | 12/2004 | Carver | |
| 2005/0023479 A1 | 2/2005 | Grodzins | |
| 2005/0024199 A1 | 2/2005 | Huey | |
| 2005/0100135 A1 | 5/2005 | Lowman | |
| 2005/0117683 A1 | 6/2005 | Mishin | |
| 2005/0135668 A1 | 6/2005 | Polichar | |
| 2005/0157842 A1 | 7/2005 | Agrawal | |
| 2005/0169421 A1 | 8/2005 | Muenchau | |
| 2005/0198226 A1 | 9/2005 | Delia | |
| 2006/0027751 A1 | 2/2006 | Kurita | |
| 2006/0056584 A1 | 3/2006 | Allman | |
| 2006/0114477 A1 | 6/2006 | Cox | |
| 2006/0140341 A1 | 6/2006 | Carver | |
| 2006/0182221 A1 | 8/2006 | Bernhardt | |
| 2006/0249685 A1 | 11/2006 | Tanaka | |
| 2006/0257005 A1 | 11/2006 | Bergeron | |
| 2006/0284094 A1 | 12/2006 | Inbar | |
| 2007/0085010 A1 | 4/2007 | Letant | |
| 2007/0140423 A1 | 6/2007 | Foland | |
| 2007/0172129 A1 | 7/2007 | Tortora | |
| 2007/0189454 A1 | 8/2007 | Georgeson | |
| 2007/0210255 A1 | 9/2007 | Bjorkholm | |
| 2007/0228284 A1 | 10/2007 | Polichar | |
| 2007/0237293 A1 | 10/2007 | Singh | |
| 2007/0280502 A1 | 12/2007 | Paresi | |
| 2008/0037707 A1 | 2/2008 | Rothschild | |
| 2008/0048872 A1 | 2/2008 | Frank | |
| 2008/0084963 A1 | 4/2008 | Clayton | |
| 2008/0128624 A1 | 6/2008 | Cooke | |
| 2008/0159591 A1 | 7/2008 | Ruedin | |
| 2008/0170670 A1 | 7/2008 | Bhatt | |
| 2008/0198970 A1 | 8/2008 | Kirshner | |
| 2008/0205594 A1 | 8/2008 | Bjorkholm | |
| 2008/0230709 A1 | 9/2008 | Tkaczyk | |
| 2008/0260097 A1 | 10/2008 | Anwar | |
| 2008/0304622 A1 | 12/2008 | Morton | |
| 2009/0067575 A1 | 3/2009 | Seppi | |
| 2009/0086907 A1 | 4/2009 | Smith | |
| 2009/0116617 A1 | 5/2009 | Mastronardi | |
| 2009/0127459 A1 | 5/2009 | Neustadter | |
| 2009/0168964 A1 | 7/2009 | Safai | |
| 2009/0238336 A1 | 9/2009 | Akery | |
| 2009/0245462 A1 | 10/2009 | Agrawal | |
| 2009/0257555 A1 | 10/2009 | Chalmers | |
| 2009/0285353 A1 | 11/2009 | Ellenbogen | |
| 2009/0316851 A1 | 12/2009 | Oosaka | |
| 2010/0020937 A1 | 1/2010 | Hautmann | |
| 2010/0161504 A1 | 6/2010 | Casey | |
| 2010/0177868 A1 | 7/2010 | Smith | |
| 2010/0177873 A1 | 7/2010 | Chen | |
| 2010/0295689 A1 | 11/2010 | Armistead | |
| 2011/0019797 A1 | 1/2011 | Morton | |
| 2011/0019799 A1 | 1/2011 | Shedlock | |
| 2011/0038453 A1 | 2/2011 | Morton | |
| 2011/0064192 A1 | 3/2011 | Morton | |
| 2011/0075808 A1 | 3/2011 | Rothschild | |
| 2011/0204243 A1 | 8/2011 | Bendahan | |
| 2011/0235777 A1 | 9/2011 | Gozani | |
| 2011/0266643 A1 | 11/2011 | Engelmann | |
| 2012/0099710 A1 | 4/2012 | Kotowski | |
| 2012/0104276 A1 | 5/2012 | Miller | |
| 2012/0116720 A1 | 5/2012 | Klann | |
| 2012/0288060 A1 * | 11/2012 | Beneke | G01V 5/0008 378/57 |
| 2013/0001048 A1 | 1/2013 | Panesar | |
| 2014/0185771 A1 | 7/2014 | Morton | |
| 2014/0192954 A1 | 7/2014 | Hanley | |
| 2014/0197321 A1 | 7/2014 | Bendahan | |
| 2015/0036798 A1 | 2/2015 | Morton | |
| 2015/0078519 A1 | 3/2015 | Morton | |
| 2015/0301220 A1 | 10/2015 | Morton | |
| 2015/0330917 A1 | 11/2015 | Morton | |
| 2015/0355117 A1 | 12/2015 | Morton | |
| 2015/0355369 A1 | 12/2015 | Morton | |
| 2016/0025888 A1 | 1/2016 | Peschmann | |
| 2016/0025889 A1 | 1/2016 | Morton | |
| 2016/0033674 A1 | 2/2016 | Allman | |
| 2016/0084984 A1 | 3/2016 | Franco | |

FOREIGN PATENT DOCUMENTS

| | | |
|---|---|---|
| EP | 1413898 A1 | 4/2004 |
| GB | 2255634 A | 11/1992 |
| GB | 2409268 A | 6/2005 |
| GB | 2424065 A | 9/2006 |

(56) References Cited

FOREIGN PATENT DOCUMENTS

| | | |
|---|---|---|
| GB | 2438317 A | 11/2007 |
| WO | 9855851 A1 | 12/1998 |
| WO | 2004010127 A1 | 1/2004 |
| WO | 2005098400 A2 | 10/2005 |
| WO | 2006036076 A1 | 4/2006 |
| WO | 2006053279 A2 | 5/2006 |
| WO | 2006078691 A2 | 7/2006 |
| WO | 2007035359 A2 | 3/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009106803 A2 | 9/2009 |
| WO | 2009143169 A1 | 11/2009 |
| WO | 2011069024 A1 | 6/2011 |
| WO | 2011091070 A2 | 7/2011 |
| WO | 2013116549 | 8/2013 |
| WO | 2013119423 A1 | 8/2013 |
| WO | 2014107675 | 7/2014 |
| WO | 2014121097 A1 | 8/2014 |
| WO | 2014124152 A2 | 8/2014 |
| WO | 2016011205 | 1/2016 |

OTHER PUBLICATIONS

International Search Report for PCT/US14/56652, dated Apr. 27, 2015.
International Search Report for PCT/US14/14198, dated May 16, 2014.
International Preliminary Report on Patentability for PCT/US2014/014198, dated Aug. 4, 2015.
International Search Report for PCT/US11/21758; dated Jul. 7, 2011, Rapiscan Systems Inc.
International Preliminary Report on Patentability for PCT/US11/21758, dated Jul. 7, 2011.
Written Opinion on Patentability for PCT/US11/21758; dated Jul. 7, 2011; Rapiscan Systems.
Molchanov P A et al: 'Nanosecond gated optical sensors for ocean optic applications' Sensors Applications Symposium, 2006. Proceedings of the 2006 IEEE Houston, Texas,USA Feb. 7-9, 2006, Piscataway, NJ, USA,IEEE, Feb. 7, 2006 (Feb. 7, 2006), pp. 147-150, XP010917671 ISBN: 978-0-7803-9580-0.
Mobile X-Ray Inspection Systems, Internet Citation, Feb. 12, 2007, pp. 1-2, URL:http://web.archive.org/web/20070212000928/http://www.bombdetecti- on.com/cat--details.php?catid=20.
International Search Report for PCT/GB09/00575, dated Apr. 7, 2010.
International Search Report for PCT/GB2009/000497, dated Jan. 22, 2010.
Smith C. R. et al: 'Application of 450 kV computed tomography to engine blocks with steel liners' Materials Evaluation vol. 65, No. 5, 2007, pp. 458-461, XP055108238.
International Search Report for PCT/US13/23676, dated Jun. 28, 2013.
International Search Report for PCT/US13/24191, Rapiscan Systems Inc., dated Jun. 25, 2013.
International Search Report for PCT/US2014/010370, dated May 13, 2014.
International Search Report for PCT/US10/58809; Rapiscan Systems Inc.; dated Apr. 19, 2011.
International Search Report for PCT/US2014/015126, dated May 27, 2014.
Written Opinion of the International Searching Authority for PCT/US2014/015126, dated May 27, 2014.

* cited by examiner

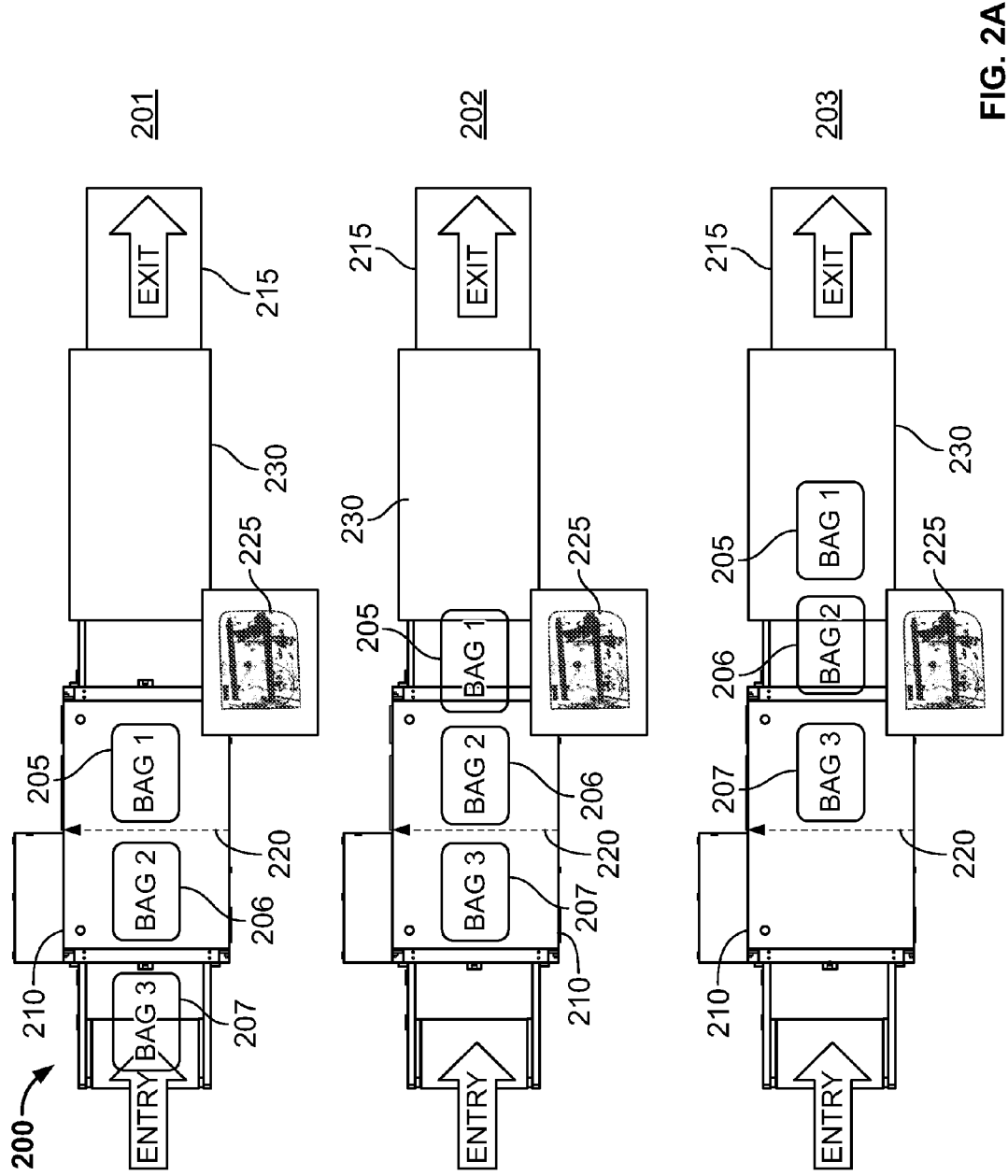

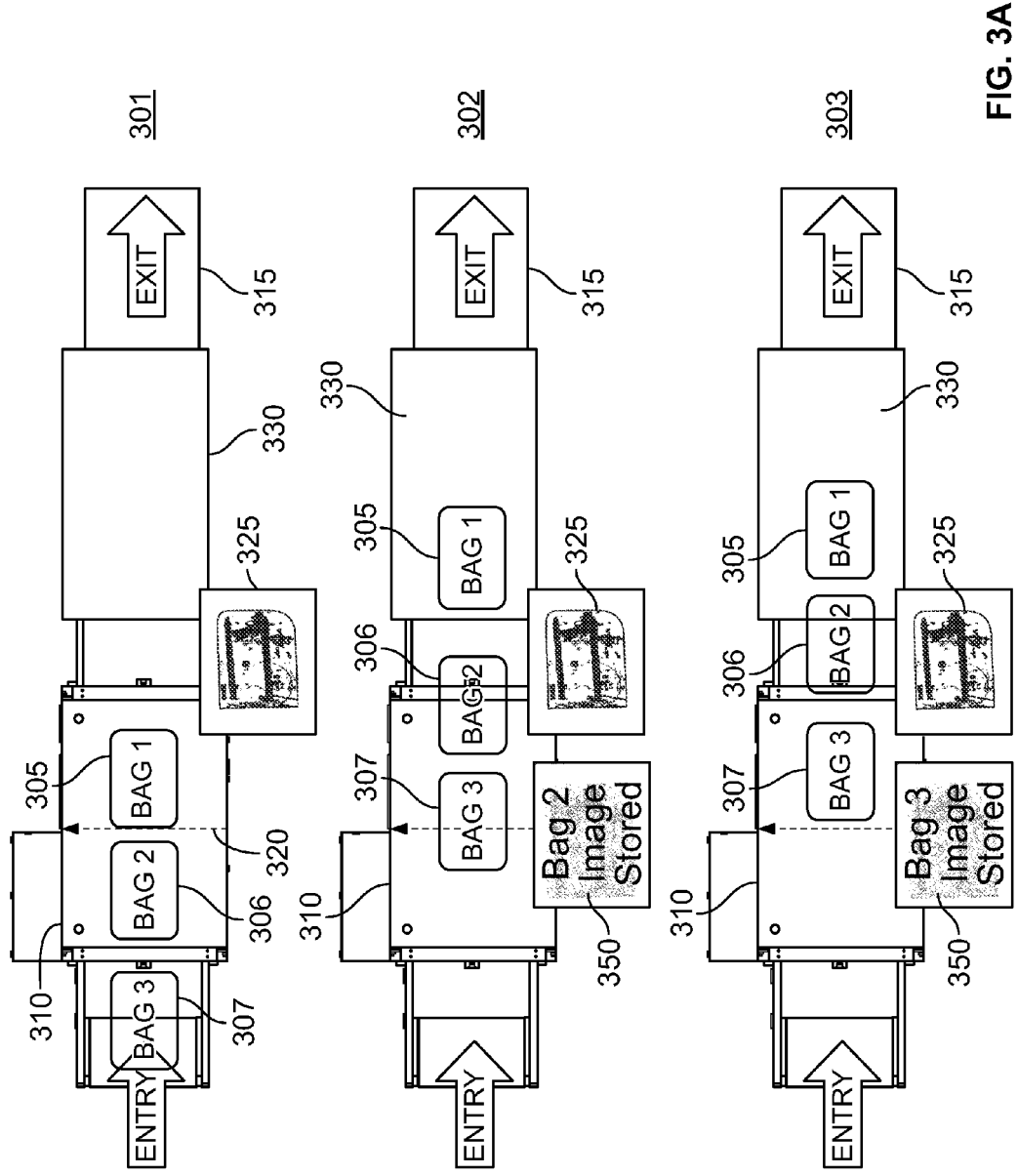

| | IMPROVEMENT | BPH | NOTES |
|---|---|---|---|
| BASELINE | | 300 | |
| IMAGE SEPARATION | 18% | 350 | ALL ARTICLES |
| STOP DELAY (EMBODIMENT 1) | 10% | 410 | 60% ARTICLES |
| STOP DELAY 2 (EMBODIMENT 2) | 13% | 445 | 60% ARTICLES |

FIG. 4

METHODS FOR IMPROVING PROCESSING SPEED FOR OBJECT INSPECTION

CROSS-REFERENCE

The present application relies upon, for priority, U.S. Provisional Patent Application No. 61/857,688, entitled "Methods for Improved Processing Speed for Object Inspection", and filed on Jul. 23, 2013, and is herein incorporated by reference in its entirety.

FIELD

The present invention relates to methods and systems for inspecting objects by means of penetrating radiation, where objects are conveyed through the penetrating radiation and subsequent images of objects are reviewed by an operator.

BACKGROUND

X-ray scanning systems have been used for visually inspecting the contents of containers and the inside of enclosed objects quickly compared to the tedious process of manually opening and inspecting an object's contents. In many cases, this improved method of inspection expedites the process and saves time and money for the users of these scanning systems. In some applications, the speed of inspection is a critical parameter that is often a balance between inspection quality, cost, and throughput (or number of objects inspected per minute).

Operator efficiency can be measured as the ratio of image review time versus the total time spent at the operator control station. All tasks not directly supporting image review result in inefficiencies, thereby reducing throughput.

To avoid confusion it is necessary to isolate and associate the image with the suspect article. In current X-ray inspection systems, a queuing conveyor is associated with the main conveyor that transmits the object through the X-ray inspection system. The purpose of the queuing conveyor is to create a physical separation between articles. A physical separation between articles allows for photo-sensor logic to identify discrete articles. Since, the queuing conveyor runs at a slower speed compared to the main conveyor, the speed of the queuing conveyor dictates the throughput of the system.

Image operators must inspect complex images while the image is stationary; thus, the operator may have to stop additional images from being generated on-screen in order to inspect existing images more thoroughly. Currently, to stop the image, the operator invokes a belt stop process. When the belt stops no additional image data is acquired or collected. Current methods usually synchronize the conveyance of objects with the operator's commands to start and stop the images. Due to mechanical and electro-optical limitations of these systems, this synchronization creates delays as the system needs to perform a recovery procedure from each "stop-to-start" transition. This usually results in system latency. Typically, this involves reversing the conveyance mechanism sufficiently and then returning to a constant forward speed to allow the conveyance and electro-optical systems to return to the previous steady state conditions that determine critical inspection quality standards. Therefore, to ensure seamless image presentation, current systems conduct a back-belt process that requires the conveyor belt to reverse for 0.75 seconds before the belt goes forward and X-rays are generated again. This incurs a 1.5 second delay from the time the image operator presses the forward or resume button on the control panel and time that image data appears once again on the display.

What is therefore needed is a system that decouples the synchronization between cessation of image generation on the display and image acquisition through conveyance of the article. Also needed are methods for compensating for image acquisition inefficiencies involving article separation by the queuing conveyor and the post-stop back belt process, so that throughput is enhanced.

SUMMARY

The present invention provides a method of inspecting an object translated forward on a conveyor through an X-ray inspection system wherein the object is scanned with penetrating radiation to generate scan image data for display on a viewing device such that the scan image data initially scrolls in synchronization with the movement of the object. The method can include stopping scrolling of the scan image data on the viewing device by an operator to examine said scan image data; asynchronously continuing the forward movement of the conveyor for a buffer time $B_t$ to collect additional image data of an object while the operator is examining said scan image data; stopping the scan process after the buffer time $B_t$ is over; storing the acquired additional image data in a buffer memory until the scan process is started again; and displaying the buffered image data on a viewing device upon restarting the scan process.

The present invention also provides a method of inspecting an object translated forward on a conveyor through an X-ray inspection system wherein the object is scanned with penetrating radiation to generate scan image data for display on a viewing device, such that the scan image initially scrolls in synchronization with the movement of the object. The method can include stopping scrolling of the scan image data on the viewing device by an operator to examine said scan image data; asynchronously continuing the forward movement of the conveyor to collect additional image data of at least one queued object while the operator is examining said scan image data; storing said acquired additional image data of the at least one queued object in a memory until scrolling of scan image data is started again; and displaying said additional image data of the at least one queued object on a viewing device upon restarting scrolling of scan image data.

The present invention further provides an X-ray inspection system for scanning an object being moved forward there through on a conveyor and displaying scan image data of the object on a viewing device such that the scan image data initially scrolls in synchronization with the movement of the object. The X-ray inspection system is operable in accordance with a method comprising: stopping scrolling of the scan image data on the viewing device by an operator to examine said scan image data; asynchronously continuing the forward movement of the conveyor for a buffer time $B_t$ to collect additional image data of an object while the operator is examining said scan image data; stopping the scan process after the buffer time $B_t$ is over; storing said acquired additional image data in a buffer memory until the scan process is started again; and displaying said buffered image data on a viewing device upon restarting the scan process.

The present invention further provides an X-ray inspection system for scanning an object being moved forward there through on a conveyor and displaying scan image data of the object on a viewing device such that the scan image data initially scrolls in synchronization with the movement of the object. The X-ray inspection system can be operated in accordance with a method comprising: stopping scrolling of the scan image data on the viewing device by an operator to examine said scan image data; asynchronously continuing the forward movement of the conveyor to collect additional image data of at least one queued object while the operator is examining said scan image data; storing said acquired additional image data of the at least one queued object in a memory until scrolling of scan image data is started again; and displaying said additional image data of the at least one queued object on a viewing device upon restarting the scrolling of scan image data.

The present invention still further provides a method of inspecting at least one object being moved forward on a conveyor through an X-ray inspection system wherein a first object is scanned with penetrating radiation to generate scan image data for display on a viewing device such that the scan image data initially scrolls in synchronization with the movement of the first object. The method can comprise: stopping scrolling of the scan image data on the viewing device by an operator to examine said scan image data of said first object; asynchronously continuing the forward movement of the conveyor for a buffer time $B_t$ to collect additional image data of a second object while the operator is examining said scan image data of said first object; stopping the scan process after collecting image data of said second object; storing said acquired additional image data of a second object in a memory until the scan process is started again; and displaying said buffered image data on a viewing device upon restarting the scan process.

The present invention still further provides a method of inspecting at least one object being moved forward on a conveyor through an X-ray inspection system wherein a first object is scanned with penetrating radiation to generate scan image data for display on a viewing device such that the scan image data initially scrolls in synchronization with the movement of the first object. The method can include: stopping scrolling of the scan image data on the viewing device by an operator to examine said scan image data of said first object; asynchronously continuing the forward movement of the conveyor for a buffer time $B_t$ to collect additional image data of a second object while the operator is examining said scan image data of said first object; storing said acquired additional image data of a second object in a memory until the scrolling of scan image data is started again; repeating the steps of collecting additional image data and storing said acquired data for third through nth objects until the buffer time $B_t$ is over; and displaying said buffered image data on a viewing device upon restarting scrolling of scan image data.

The following embodiments and aspects of the invention are described and illustrated in conjunction with systems, tools and methods, which are meant to be exemplary and illustrative, not limiting in scope.

In some embodiments, the present specification is directed towards methods and/or systems for improving the speed of the inspection process with little or no impact to cost and inspection quality.

An X-ray inspection system may scan objects being conveyed through the system and subsequently, an operator may view, on a viewing device such as a monitor, generated images of the conveyed object.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 2A is a top view of an X-ray baggage inspection system being operated using a conventional method;

FIG. 3A is a top view of an X-ray baggage inspection system when operated to generate the throughput in accordance with the improved method of the present specification;

FIG. 4 is a table illustrating enhancements in throughput, when improved methods of the present invention are applied to X-ray baggage inspection systems, in accordance with one embodiment.

DETAILED DESCRIPTION

Figure 1A:
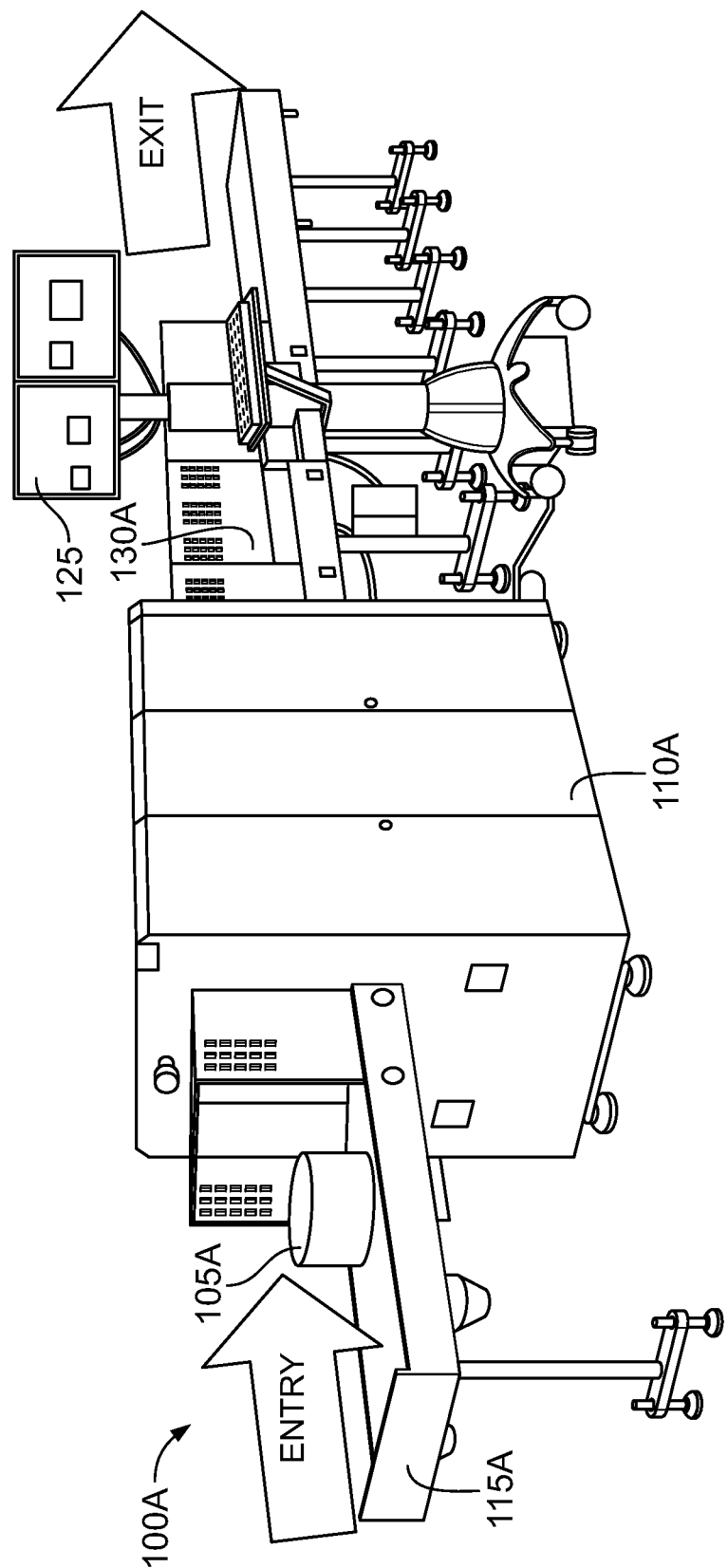
FIG. 1A is a perspective view of an exemplary X-ray baggage inspection system in accordance with an embodiment of the present invention.

In some applications, the speed of inspection is a critical parameter that is often a balance between inspection quality, cost, and throughput (also defined as the number of objects inspected per minute). In accordance with some embodiments described in the present specification, methods and/or systems are provided to improve the speed of the inspection process with little or no impact to cost and inspection quality.

An X-ray inspection system may scan objects being conveyed through the system and subsequently, an operator may view, on a viewing device such as a monitor, generated images of the conveyed object.

In other embodiments of the present specification, the process of the operator stopping the images for further visual inspection is decoupled from the process of object conveyance and data collection for subsequent image projection. The conveyance and data collection may continue in a forward direction even after the operator has generated a stop command for the image inspection process. The images scrolling on the viewing platform, however, may stop immediately to allow the operator to perform a more thorough visual inspection. The continuation of conveyance and data collection may offer a variety of recovery processes that reduce or eliminate the typical delays of current embodiments.

The X-ray system includes a source for generating an incident beam of penetrating radiation and a plurality of detector elements that collect the radiation as it passes through the object(s) under inspection. The levels of collected radiation present information about the contents of the object including but not limited to density, material properties, size, volume and many other characteristics of the object and its contents. This information is collected via a plurality of methods including but not limited to scintillation materials of singular or multiple absorption characteristics, photodiodes—singular or stacked, analog to digital converters, and computer elements.

This information is processed via a plurality of mathematical processes to extract many characteristics of the object being scanned and for generating images of the object for subsequent display on a viewing platform. This allows the operator to distinguish the contents of an object and determine whether the object requires further review or manual inspection.

In one embodiment of the present invention, the process of the operator stopping the images for inspection is decoupled from the process of object conveyance and data collection for subsequent image projection.

In one embodiment, the conveyance and data collection continues in a forward direction even after the operator has generated a stop command for the image inspection process. The images scrolling on the viewing platform stop immediately to allow the operator to perform a more thorough inspection. The continuation of conveyance and data collection offers a variety of recovery processes that reduce or eliminate the typical delays of current embodiments.

Therefore, in an embodiment, upon initiation of stopping an image the system continues to run the conveyor belt and acquire additional image data for a minimum of 1.5 seconds. The acquired image data is stored in memory until the image operator presses the forward or resume button on the control panel, at which time buffered data is displayed without delay. The newly acquired image data is displayed immediately and permits seamless scrolling. Since the image operator invests an average of a minimum of 1.5 seconds in conducting image review, there is an immediate efficiency improvement of 1.5 seconds per stopped image.

In another embodiment, as described in the present specification, the data collection continues forward just enough to allow the system recovery time to become zero. After the operator stops scrolling of scan images, to freeze a particular image for detailed inspection, the conveyance and data collection continues forward for an appropriate amount of time. Thereafter the system discontinues radiating the object, reverses the belt and awaits the operator's start command. Upon the operator's start comments, the already collected data lines or images begin to scroll on the viewing station while the system achieves the steady state parameters it needs for quality inspection. The operator perceives a zero delay since the image scrolling stops and starts immediately with the operator's commands.

In another embodiment, the conveyance and data collection continues for a longer period, limited only by certain system variables that can be manipulated in system designs. The conveyance limits are such that the object under inspection does not escape the operator's control by exiting the system prior to completing the inspection process. Examples of system design elements that extend the duration of conveyance and data collection during the operator's inspection process are extended conveyors, shrouded exit conveyors, and similar system design elements. In this embodiment, the extra data collection can be displayed immediately upon the operator's start command or managed by intelligent software algorithms to display the data in a variety of methods including but not limited to, a fast scroll of data to catch up to the live data acquisition, displaying a portion of the acquired data based on each object, presenting object images only when the entire object is scanned, and having stopped images always for the operator's inspection with minimal or no time wasted in scrolling.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

One of ordinary skill in the art should appreciate that the features described in the present application can operate on any computing platform including, but not limited to: a laptop or tablet computer; personal computer; personal data assistant; cell phone; server; embedded processor; digital signal processor (DSP) chip or specialized imaging device capable of executing programmatic instructions or code.

It should further be appreciated that the platform provides the functions described in the present application by executing a plurality of programmatic instructions, which are stored in one or more non-volatile memories, using one or more processors and presents and/or receives data through transceivers in data communication with one or more wired or wireless networks.

It should further be appreciated that each device has wireless and wired receivers and transmitters capable of sending and transmitting data, at least one processor capable of processing programmatic instructions, memory capable of storing programmatic instructions, and software comprised of a plurality of programmatic instructions for performing the processes described herein. Additionally, the programmatic code can be compiled (either pre-compiled or compiled "just-in-time") into a single application executing on a single computer, or distributed among several different computers operating locally or remotely to each other.

Figure 1B:
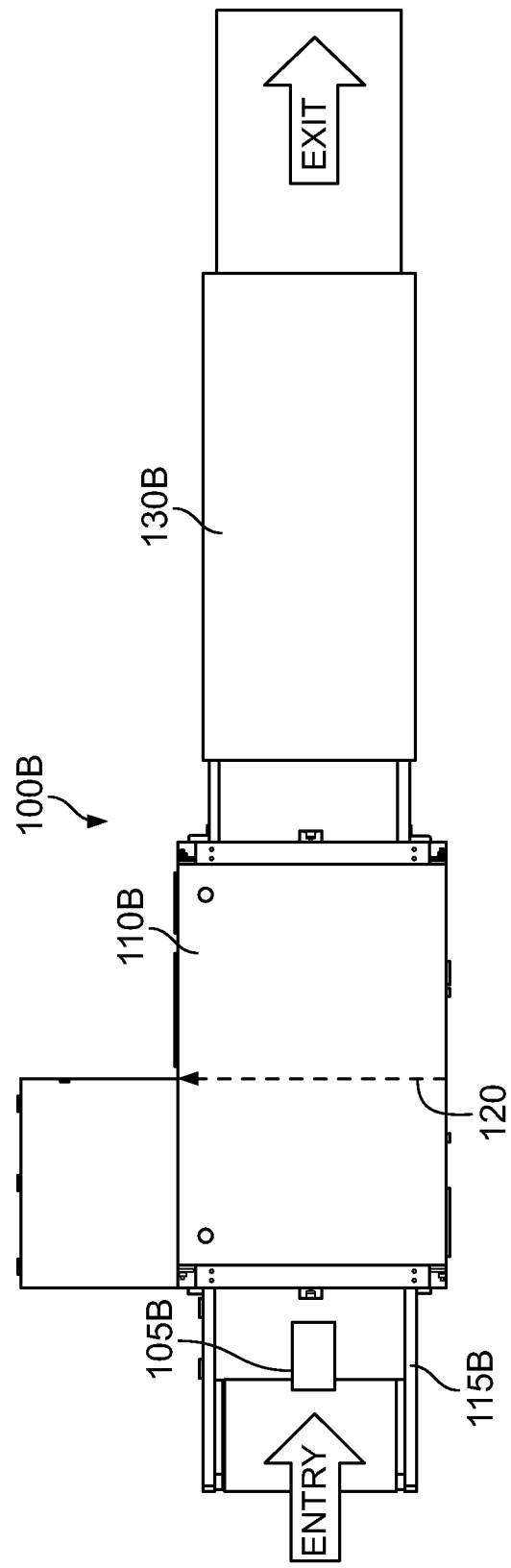
FIG. 1B is a top view of the X-ray baggage inspection system of FIG. 1A.

FIGS. 1A and 1B show, respectively, in accordance with an embodiment, skewed perspective and top views of an X-ray baggage inspection system. Referring to FIGS. 1A and 1B simultaneously, in X-ray baggage inspection system 100A, 100B, objects 105A, 105B, such as baggage, are translated on a conveyor 115A, 115B through a baggage scanning enclosure 110A, 110B. The baggage scanning enclosure 110A, 110B comprises an X-ray source and a plurality of detector elements. The X-ray source irradiates the conveyed objects 105A, 105B with penetrating radiation 120 while the plurality of detector elements collect the radiation transmitted through the objects 105A, 105B. The levels of collected radiation are processed using a computer to generate and store, if required, scanned images of the conveyed objects 105A, 105B. The scanned images are presented onto a viewing device, such as a monitor 125, for an operator to review/examine the scanned images. Subsequently, if the operator desires to physically inspect contents of a scanned object 105A, 105B, based on the operator's review of the corresponding scanned images, the operator can do so by having the conveyor 115A, 115B stop at an appropriate time to enable accessing the scanned object 105A, 105B through an access area 130A, 130B. An exemplary implementation of the X-ray baggage inspection system 100A, 100B is the Rapiscan® 620DV system, which is a dual-view, multi-energy system, and is described at the following web site: http://www.rapiscansystems.com/en/products/bpi/productsrapiscan_620dv, which is a product that is manufactured and sold by the Applicant of the present specification.

As known to persons of ordinary skill in the art, an operator may have to stop scrolling scanned images on a monitor to inspect them more thoroughly. In conventional X-ray baggage inspection systems, the scrolling of the scanned image on the monitor is synchronous with conveyance of the corresponding scanned object through the x-ray baggage inspection system. Due to mechanical and electro-optical limitations of these prior art x-ray baggage inspection systems, this synchronization creates delays as the x-ray baggage inspection system needs to perform a recovery procedure from each "stop-to-start" transition. Typically, this involves reversing the conveyance mechanism sufficiently and then returning to a constant forward speed to allow the conveyance and electro-optical systems to return to the previous steady state conditions that determine critical inspection quality standards, such as, but not limited to image quality and any other latency issues.

FIG. 2A shows a top view of an X-ray baggage inspection system 200 that is fully queued up with objects/baggage 205, 206 and 207 on conveyor 215 and wherein scrolling of a scanned image on monitor 225 is synchronous with conveyance of a corresponding scanned object/baggage 205, 206, and 207, in accordance with a conventional method of operation of the x-ray baggage inspection system 200. During operation, baggage 205 is conveyed through the baggage scanning enclosure 210 to synchronously generate corresponding scanned image of baggage 205 on the monitor 225. At step 201, once the baggage 205 has moved just ahead of the last X-ray scanning beam 220 (so that a complete scanned image of the baggage 205 has been generated), an operator stops the conveyor 215 to simultaneously stop the synchronous scrolling of the scanned image on the monitor 225 and enable the operator to review/examine the now stationary scanned image of the baggage 205.

After examining the scanned image of the baggage 205, if the operator decides to physically inspect the baggage 205 he must typically restart the conveyor 215 and wait for the baggage 205 to reach the access area 230. As discussed earlier, this "stop-to-start" transition causes time delay (latency) due the system recovery procedure. Step 202 shows this situation where the operator has restarted the conveyor 215 so that the baggage 205 is now being conveyed towards the access area 230. However, as a result of synchronization or coupling of the movement of the conveyor 215 with the generation and scrolling of the scanned image (on the monitor 225) of the next queued-up baggage 206, the operator is now burdened with an additional pending task of examining the scanned image of baggage 206 which is being presented on the monitor 225 while baggage 205 is still on its way to reach the access area 230.

Thus, at step 203, by the time the baggage 205 eventually reaches the access area 230, as a result of synchronicity of the movement of the conveyor 215 with the generation and scrolling of the scanned image (on the monitor 225) of the queued-up baggage 206, 207 the operator now has additional pending tasks of with reference to the scanned images of baggage 206, 207 as well as physical inspection of the baggage 205 that has now reached the access area 230.

Therefore, the overall screening time and as a result, the throughput of such conventional X-ray baggage inspection systems is typically a summation of at least an object scan data collection time '$S_t$,' operator review time of the presented scanned image including the operator's time to inspect and decide on the threat level of the scanned object '$D_t$' and the inspection system recovery time '$R_t$' from a "stop-to-start" transition.

Figure 2B:
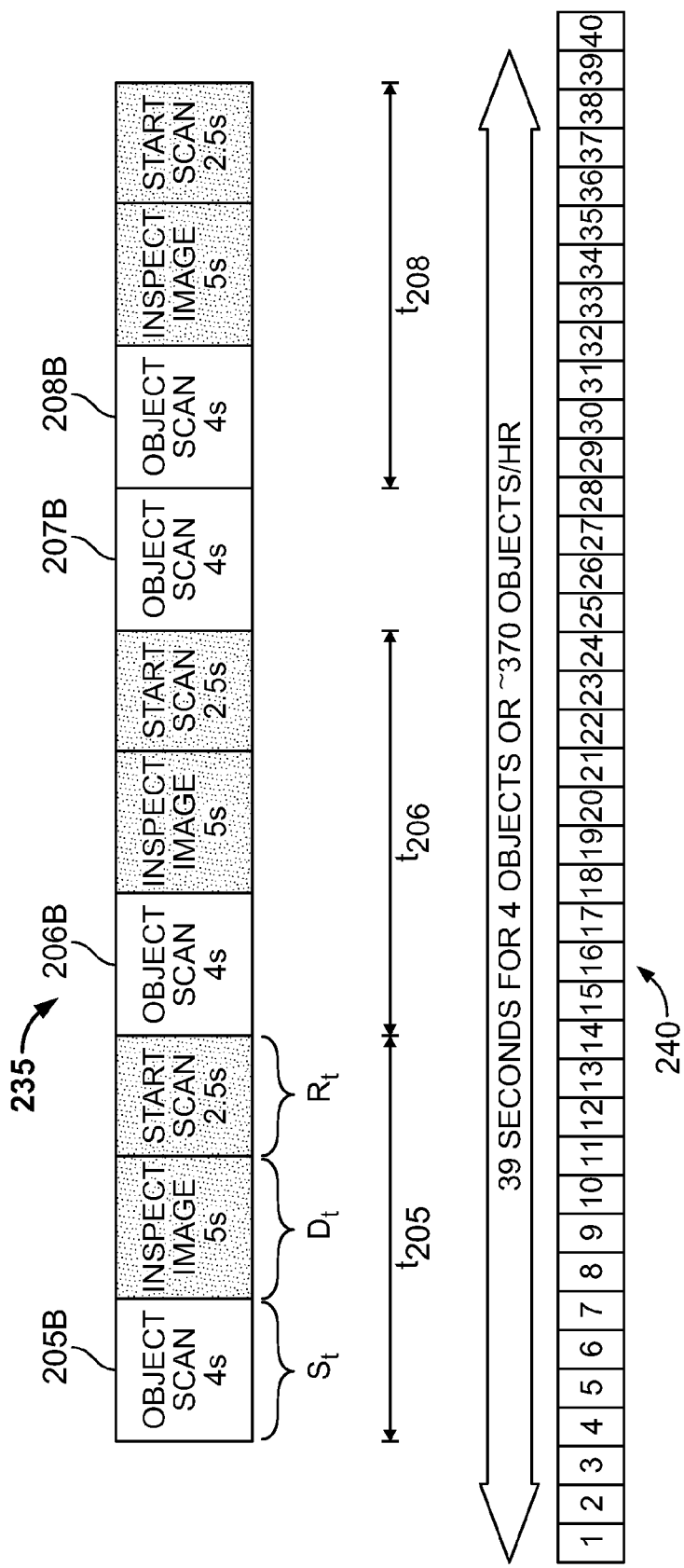
FIG. 2B is a schematic timeline diagram showing throughput of the X-ray baggage inspection system of FIG. 2A when operated using a conventional method.

FIG. 2B shows an overall throughput calculation when the x-ray baggage inspection system 200 of FIG. 2A is operated in accordance with the conventional method, wherein scrolling of a scanned image on monitor 225 is synchronous with conveyance of a corresponding scanned object through the x-ray baggage inspection system 200. Referring to FIG. 2B, in accordance with an embodiment, the scale 235 shows time constituents involved in the overall screening/inspection operation and therefore the throughput of the x-ray baggage inspection system 200 when three (205B, 206B, 208B) out of four objects 205B, 206B, 207B and 208B are also being physically inspected by the operator, besides reviewing their scanned images. The throughput calculation assumes that the object scan data collection time $S_t$, for an average 2.5 foot long object/baggage, is approximately 4 seconds, operator review/decision time of the presented scanned image $D_t$ is on an average about 5 seconds while the x-ray baggage inspection system recovery time $R_t$ from a "stop-to-start" transition is approximately 2.5 seconds. Correspondingly, scale 240 shows the total time being spent in scanning the four objects 205B, 206B, 207B, and 208B when the scrolling of the scanned images for three out of the four objects is stopped by the operator. As a result, the x-ray baggage inspection system 200 takes a total of about 39 seconds to scan four queued objects 205B, 206B, 207B, and 208B with the scrolling of the scanned images for three of them being required to be stopped for examination/review by the operator. Times $t_{205}$, $t_{206}$, $t_{208}$ include examination/review of the scanned images of the objects 205B, 206B and 208B by the operator. The scrolling of the scanned image of the scanned object 207B is not stopped by the operator for review/examination. Therefore, the throughput of system is about 370 objects per hour.

Figure 3B:
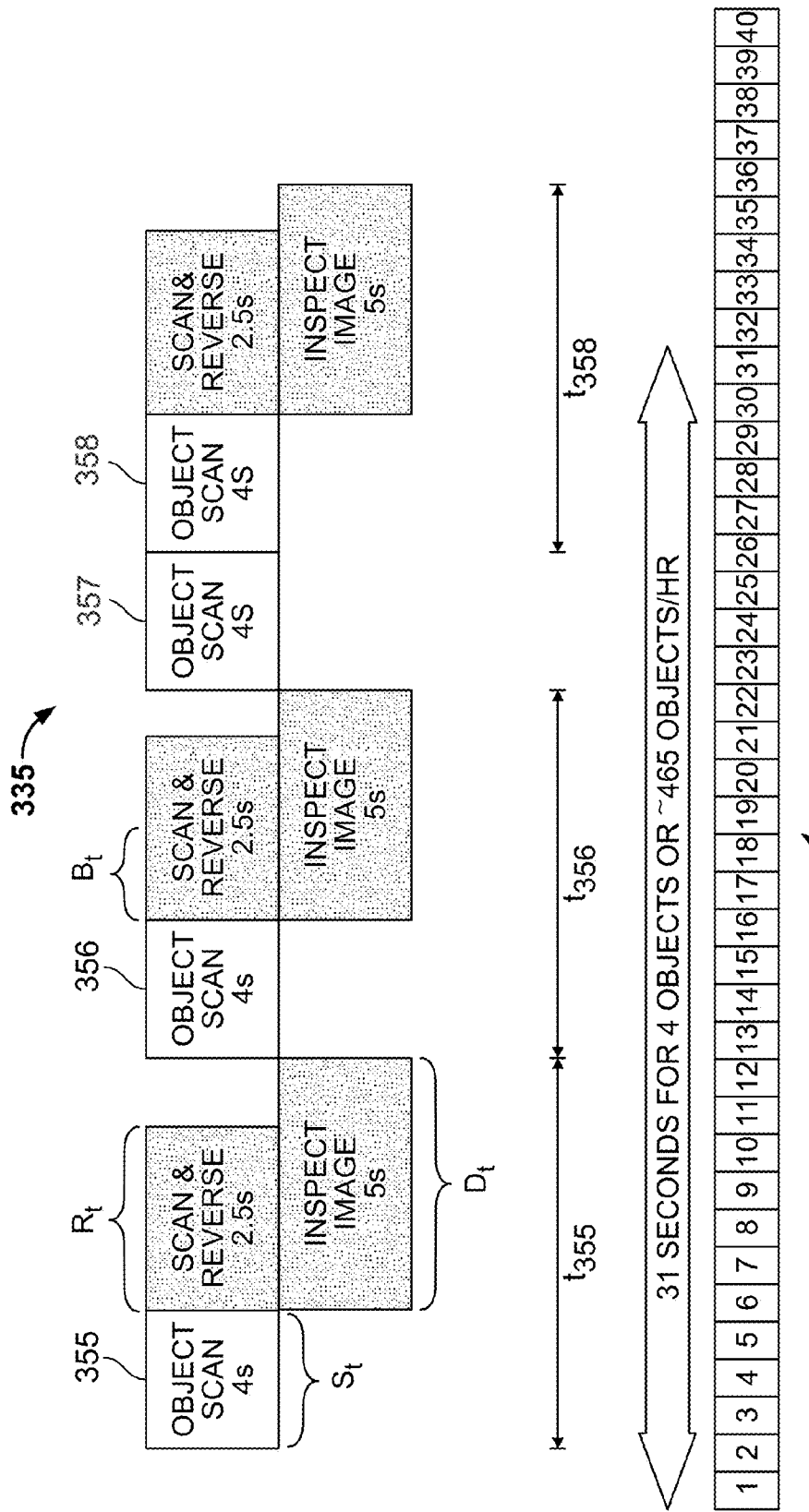
FIG. 3B is a schematic timeline diagram showing improved throughput of the X-ray baggage inspection system when operated in accordance with one embodiment of the method of the present specification.

FIG. 3A shows a top view of an X-ray baggage inspection system 300 that is fully queued up with objects/baggage 305, 306 and 307 on conveyor 315 and is being operated in accordance with the improved method that enables higher throughput with continuous scan image data collection, as described below with reference to FIGS. 3B and 3C. Referring to FIG. 3A, during operation, baggage 305 is conveyed through the baggage scanning enclosure 310 to generate corresponding scanned image of baggage 305 on the monitor 325. At step 301, once the baggage 305 has moved just ahead of the last X-ray scanning beam 320 (so that a complete scanned image of the baggage 305 has been generated), an operator stops the scrolling of the scanned image on the monitor 325 to enable the operator to review/examine the now stationary scanned image of the baggage 305. However, in accordance with the improved method of operation of the present invention, the stopping of the scrolling of the scanned image of the object 305 does not result in a synchronous stopping of the conveyor 315. In fact, the conveyor 315 continues to move forward and collect and store scanned image data of the subsequent queued object 306 while the operator examines/reviews the scanned image of the object 305.

As shown in step 302, if the operator continues to examine/review the scanned image of the object 305, other objects 306 and 307 continue to be scanned and scan data is stored in buffer memory 350 for subsequent display to the operator. In one embodiment, objects 306 and 307 in the queue continue to be scanned until a decision regarding the benignity of the object 305 is made by the operator or until the object 305 reaches the access area 330. Therefore, the object 305 gets closer and closer to the access area 330 such that if the operator decides to physically inspect the contents of the object 305 little or no time is spent waiting for the object 305 to reach the access area 330. In one embodiment, the conveyor 315 continues to move forward and queued objects 306 and 307 are scanned for a buffer time, $B_t$, after which the scan process is stopped until the operator restarts it. In one embodiment, buffer time, $B_t$ is a fraction of the system recovery time $R_t$ from a "stop-to-start" transition.

At step 303, when the object 305 has reached the access area 330 the stored scanned image data of the queued object 306 is immediately available for review/examination by the operator, the object 306 is already on its way to the access area 330 and also the scanned image data of the subsequent object 307 is collected and stored in the buffer memory 350.

FIG. 3B shows an overall throughput calculation when the x-ray baggage inspection system 100, described in FIGS. 1A and 1B, is operated in accordance with an improved method, described above with reference to FIG. 3A, that enables high throughput by minimizing or eliminating the inspection system recovery time $R_t$ as perceived by the operator and resulting from the "stop-to-start" transitions (delayed image stop or stop delay). Referring to FIG. 3B, in accordance with an embodiment, the scale 335 shows time constituents involved in the overall screening/inspection operation and therefore the throughput of the x-ray baggage inspection system 300, when scrolling of the scanned images for three out of four queued up objects 355, 356, 357 and 358 is stopped for review/examination by the operator. In accordance with an example, it is assumed that the object scanned data collection time $S_t$, for an average 2.5 foot long object/baggage, is approximately 4 seconds, operator review time of the presented scanned image $D_t$ is on an average about 5 seconds while the inspection system recovery time $R_t$ from a "stop-to-start" transition is approximately 2.5 seconds.

By way of example, during operation, when the operator is presented with the scanned image of object 355 the operator stops the scrolling of the scanned image for examination/review. However, in accordance with the improved method, stopping of the scrolling of the scanned image of object 355 does not result in an immediate synchronized stopping of the conveyor 315. In fact, the conveyor 315 is enabled to continue to move for a buffer period of time $B_t$ thereby enabling collection of buffer scanned data, equivalent to the time $B_t$, of the next queued up object 356 while the operator is examining the stationary scanned image of object 355. In other words the conveyor 315 is asynchronous or decoupled with the scrolling of the scanned image for a period of time that is a function of the buffer time $B_t$ which in turn is a function of the system recovery time $R_t$. In one embodiment, the buffer time $B_t$ is a fraction of the inspection system recovery time $R_t$. In one embodiment the buffer time $B_t$ is approximately 40 to 60%, and preferably 50% of the system recovery time $R_t$. In one embodiment the buffer time $B_t$ is approximately 1.5 seconds. After moving forward for a buffer time $B_t$, scanning of objects is stopped. Therefore, the conveyor 315 reverses and moves backwards and waits for the operator to finish examining the scanned image of the object 355. Therefore, after finishing examination, when the operator restarts the x-ray baggage inspection system 300, he is immediately presented with scrolling of scanned image representing buffer scanned data of object 356 equivalent to the buffer time $B_t$. While buffer scanned data is presented to the operator the conveyor 315 moves forward and starts generating live scanned images of the remaining portion of the object 356. Therefore, in effect, the improved method of the present invention enables the operator to perceive zero system recovery time $R_t$.

Accordingly, the scale 340 shows the total time being spent in scanning the four objects 355, 356, 357, and 358 such that the scrolling of the scanned images of three out of the four objects is stopped by the operator. As a result, the x-ray baggage inspection system 300 takes a total of about 31 seconds to scan four queued objects 355, 356, 357, and 358, with the scrolling of the scanned images of three of them being required to be stopped for examination/review by the operator. Times $t_{355}$, $t_{356}$, $t_{358}$ include examination/review of the scanned images of the objects 355, 356 and 358 by the operator. The scrolling of the scanned image of the scanned object 357 is not stopped by the operator for review/examination. Therefore, the improved throughput of system is about 465 objects per hour.

In one embodiment, the concept of delayed image stop is further expanded to take advantage of the additional 3.5 seconds (after the buffer time $B_t$ is over) spent in inspecting the stationary image. Additional objects continue to be scanned while the image display is halted. In one embodiment, the x-ray baggage inspection system 300 automatically monitors the position of the object to ensure it does not exit the x-ray baggage inspection system 300 without proper disposition by the image operator. In one embodiment, when the x-ray baggage inspection system 300 is restarted, the acquired image data is immediately displayed to the image operator in a splash mode, where images are presented as discrete images, as opposed to a scrolling mode. In one embodiment, the scrolling display begins automatically to ensure seamless information presentation.

FIG. 4 is a table illustrating enhancements in throughput, when improved methods of the present invention are applied to X-ray baggage inspection systems. These throughput enhancements are based on a theoretical model with average bag lengths and average image review times, with throughput being measured in bags per hour (BPH). Referring to FIG. 4, there is an 18% improvement in the image separation process 401, using the methods of the present invention. When the conveyor 315 is kept moving for a buffer time $B_t$, while the operator stops scrolling of images to review a particular image, the improvement in throughput during stop-delay 402 is about 10%. When the conveyor 315 is kept moving for the entire length of time while the operator stops scrolling of images to review a particular image, the improvement in throughput during stop-delay 403 is about 13%. It has been seen that up to 485 seconds (8 minutes) of image acquisition time could be recovered by queuing object images in the buffer during image review, resulting in a 13% improvement for stopped images under ideal circumstances.

Figure 5:
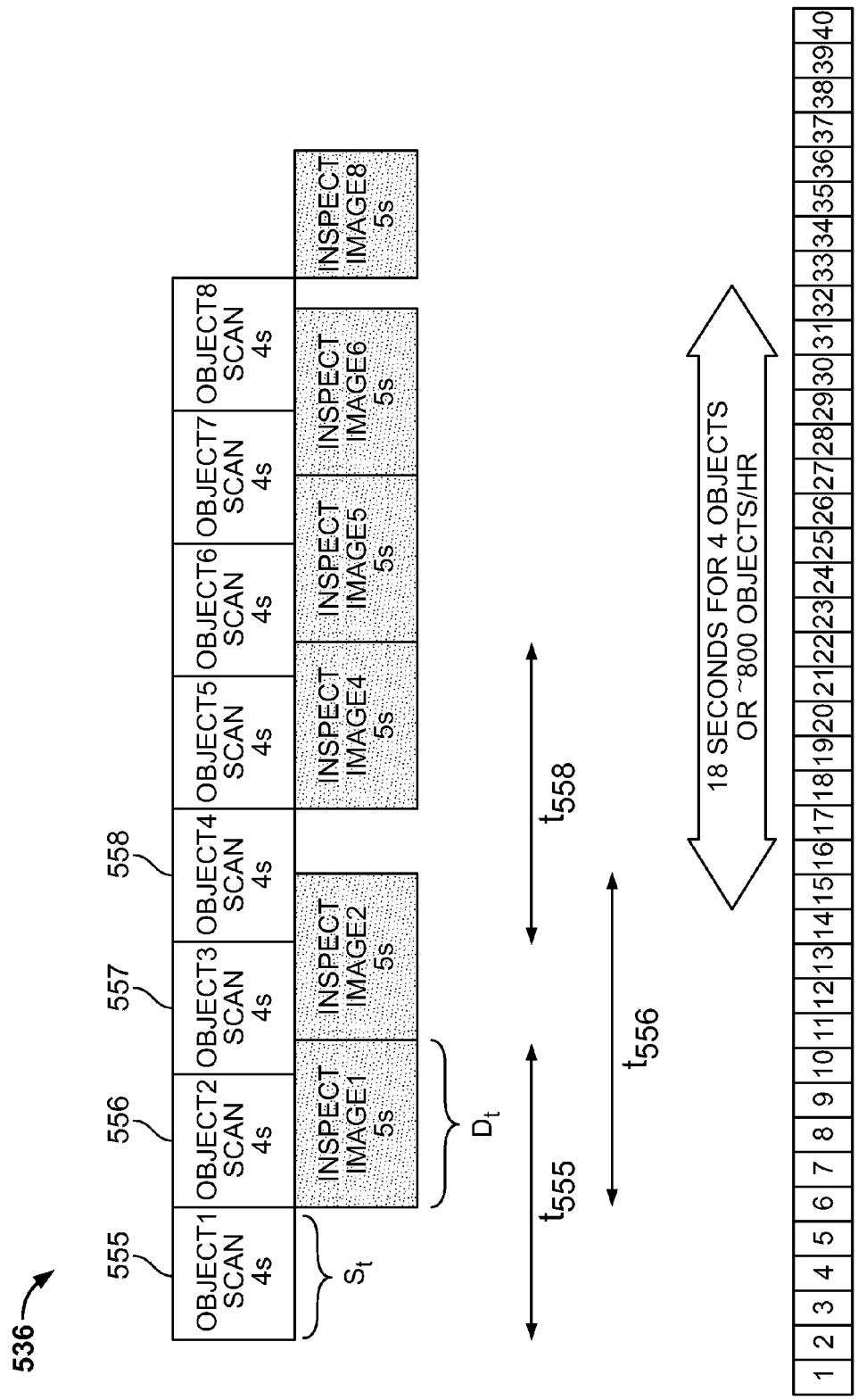
FIG. 5 is a schematic timeline diagram showing improved throughput of the X-ray baggage inspection system when operated in accordance with one embodiment of the method of the present specification.

FIG. 5 shows an overall throughput calculation when the x-ray baggage inspection system 300 is operated in accordance with another improved method that enables higher throughput with continuous scanned image data collection. In accordance with an embodiment, the scale 536 shows time constituents involved in the overall screening/inspection operation and therefore the throughput of the x-ray baggage inspection system 300 when scrolling of the scanned images of three out of four queued up objects 555, 556, 557 and 558 is stopped for review/examination by the operator. In accordance with an example, it is assumed that the object scanned data collection time $S_t$, for an average 2.5 foot long object/baggage, is approximately 4 seconds and the operator review time of the presented scanned image $D_t$ is on an average about 5 seconds. The present method of operation completely eliminates the system recovery time $R_t$ since the conveyor 315 is enabled to move continuously for scanned data collection without any real "stop-to-start" transitions.

During operation, when the operator is presented with the scanned image of object 555 he stops the scrolling of the scanned image for examination/review. However, in accordance with the improved method, stopping of the scrolling of the scanned image of object 555 does not result in an immediate synchronized stopping of the conveyor 315. In fact, the conveyor 315 is enabled to continue to move forward so that scanned data collection of the subsequent queued up objects continues unabated and stored/buffered in an electronic memory 350. In accordance with an embodiment, the scanned data collection continues and the conveyor 315 also continues to move for at least a time period equivalent to the operator's average decision/review time $D_t$. In one embodiment, the scanned data collection and the conveyor 315 stop only when the object 555 approaches the access area 330 (shown in FIG. 3A) if the operator decides to physically inspect the contents of the object 555. At the end of the operator review/decision time $D_t$ when the operator restarts the x-ray baggage inspection system 300 he is immediately presented with scrolling of scanned image representing buffered/stored scanned data of the subsequently queued up object 556. In one embodiment, the operator is presented with the entire buffered/stored scanned image of the object 556 while in another embodiment the currently displaying scanned image of the object 555 is moved in accelerated scrolling or fast-forward mode to display the buffered/stored scanned image of the object 556.

Accordingly, the scale 541 shows the total time being spent in scanning the four objects 555, 556, 557, and 558 such that the scrolling of the scanned images of three out of the four objects is stopped by the operator for review/examination. As a result, the x-ray baggage inspection system 300 takes a total of about 18 seconds to scan four queued objects 555, 556, 557, and 558 with the scrolling of the scanned images of three of them being required to be stopped for examination/review by the operator. Times $t_{555}$, $t_{556}$, $t_{558}$ include both data acquisition time and examination/review time of the scanned images of the objects 555, 556 and 558 by the operator, and thus overlap due to the simultaneous nature of examination/review of one object and data acquisition of a subsequent object. In one embodiment, examination/review time is always 5 seconds. The scrolling of the scanned image of the scanned object 557 is not stopped by the operator for review/examination. Therefore, the improved throughput of x-ray baggage inspection system 300 is up to about 800 objects per hour.

It should be understood by those of ordinary skill in the art that the methods of the present specification can be employed with any inspection system in which an object under inspection is translated as images are collected. Thus, the inspection system of the present invention is not limited to a baggage screening system, but rather, may also be used with a cargo inspection system, aircraft and other vehicle inspection system, etc. In addition, the methods of the present specification may be used with an inspection system regardless of size or overall footprint. Further, it should be noted herein that the conveying mechanism can be any mechanism for translating an object through an inspection volume, including, but not limited to a conveyor belt; a tractor/trailer; a vehicle towing mechanism; a line; a cable; a movable platform; and the like.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of inspecting an object translated forward on a conveyor through an X-ray inspection system, wherein the object is scanned with penetrating radiation to generate scan image data of the object for display on a viewing device such that the scan image data of the object initially scrolls in synchronization with a forward movement of the object, the method comprising:
   stopping scrolling of the scan image data of the object on the viewing device by an operator to examine said scan image data of the object;
   asynchronously continuing the forward movement of the conveyor for a buffer time $B_t$ to perform a scan process, wherein the scan process collects additional scan image data of the object while the operator is examining said scan image data of the object;
   stopping the scan process after the buffer time $B_t$ is over, wherein the buffer time $B_t$ is a function of a system recovery time $R_t$ and wherein the system recovery time $R_t$ is the time from stopping a scan to starting a scan;
   storing the additional scan image data of the object in a buffer memory to create a buffered image data of the object until the scan process is started again; and
   displaying the buffered image data of the object on the viewing device upon restarting the scan process.

2. The method of claim 1, wherein said buffer time $B_t$ is 40% to 60% of the system recovery time $R_t$.

3. The method of claim 1, wherein said buffer time $B_t$ is approximately 1.5 seconds.

4. The method of claim 1, wherein said X-ray inspection system comprises a baggage inspection system.

5. A method of inspecting an object translated forward on a conveyor through an X-ray inspection system, wherein the object is scanned with penetrating radiation to generate scan image data of the object for display on a viewing device, such that the scan image data of the object initially scrolls in synchronization with a forward movement of the object, the method comprising:
   stopping scrolling of the scan image data of the object on the viewing device by an operator to examine said scan image data of the object;
   asynchronously continuing the forward movement of the conveyor for a buffer time $B_t$ to collect additional scan image data of at least one queued object while the operator is examining said scan image data of the object, wherein the buffer time $B_t$ is a function of a recovery time $R_t$ from stopping a scan to starting a scan;
   storing said additional scan image data of the at least one queued object in a memory until scrolling of scan image data of the object is started again; and
   displaying said stored additional scan image data of the at least one queued object on the viewing device upon restarting scrolling of scan image data of the object.

6. The method of claim 5, wherein asynchronously continuing the forward movement of the conveyor to collect additional scan image data of at least one queued object comprises asynchronously continuing the forward movement of the conveyor for a time period of approximately 1.5 seconds.

7. The method of claim 5, wherein said X-ray inspection system comprises a baggage inspection system.

8. A method of inspecting at least one object being moved forward on a conveyor through an X-ray inspection system, wherein a first object is scanned with penetrating radiation to generate scan image data of the first object for display on a viewing device such that the scan image data of the first object initially scrolls in synchronization with a forward movement of the first object, the method comprising:
　　stopping scrolling of the scan image data of the first object on the viewing device by an operator to examine said scan image data of said first object;
　　asynchronously continuing the forward movement of the conveyor for a buffer time $B_t$ to perform a scan process, wherein the scan process collects additional scan image data of a second object while the operator is examining said scan image data of said first object, wherein the buffer time $B_t$ is a function of a system recovery time $R_t$, and wherein the system recovery time $R_t$ is the time from stopping a scan to starting a scan;
　　stopping the scan process after collecting the additional scan image data of said second object;
　　storing said additional scan image data of the second object in a memory until the scan process is started again; and
　　displaying said stored additional scan image data of the second object on the viewing device upon restarting the scan process.

9. The method of claim 8, wherein asynchronously continuing the forward movement of the conveyor for a buffer time $B_t$ to collect additional scan image data of a second object comprises asynchronously continuing the forward movement of the conveyor for a time period of approximately 1.5 seconds.

10. A method of inspecting at least one object being moved forward on a conveyor through an X-ray inspection system, wherein a first object is scanned with penetrating radiation to generate scan image data of the first object for display on a viewing device such that the scan image data of the first object initially scrolls in synchronization with a forward movement of the first object, the method comprising:
　　stopping scrolling of the scan image data of the first object on the viewing device by an operator to examine said scan image data of said first object;
　　asynchronously continuing the forward movement of the conveyor for a buffer time $B_t$ to collect additional scan image data of a second object while the operator is examining said scan image data of said first object, wherein the buffer time $B_t$ is a function of a system stop to system start transition time;
　　storing said additional scan image data of the second object in a memory until the scrolling of scan image data of the first object is started again;
　　repeating the steps of collecting additional scan image data and storing said additional scan image data for a third through an nth objects until the buffer time B is over; and
　　displaying said stored additional scan image data of said third through said nth objects on the viewing device upon restarting scrolling of scan image data of the first object.

11. The method of claim 10, wherein the buffer time $B_t$ is equivalent to an operator's average decision review time $D_t$.

12. The method of claim 10, wherein the buffer time $B_t$ is approximately 5 seconds.

13. The method of claim 10, wherein asynchronously continuing the forward movement of the conveyor for a buffer time $B_t$ comprises continuing the forward movement of the conveyor until the first object reaches an access area, wherein the first object can be physically accessed.

* * * * *